(12) United States Patent
Sablone

(10) Patent No.: US 12,702,596 B2
(45) Date of Patent: Aug. 11, 2026

(54) ABSORBENT STRUCTURE FOR SANITARY ARTICLES AND METHOD FOR ITS PRODUCTION

(71) Applicant: Fameccanica.Data S.p.A., San Giovanni Teatino (IT)

(72) Inventor: Gabriele Sablone, San Giovanni Teatino (IT)

(73) Assignee: Fameccanica.Data S.p.A.

( * ) Notice: Subject to any disclaimer, the term of this patent is extended or adjusted under 35 U.S.C. 154(b) by 333 days.

(21) Appl. No.: 18/524,848

(22) Filed: Nov. 30, 2023

(65) Prior Publication Data

US 2024/0180754 A1 Jun. 6, 2024

(30) Foreign Application Priority Data

Dec. 1, 2022 (IT) ........................ 102022000024798

(51) Int. Cl.

| | |
|---|---|
| ***A61F 13/15*** | (2006.01) |
| ***A61F 13/47*** | (2006.01) |
| ***A61F 13/53*** | (2006.01) |
| ***A61F 13/534*** | (2006.01) |

(52) U.S. Cl.

CPC .. *A61F 13/15585* (2013.01); *A61F 13/15699* (2013.01); *A61F 13/47* (2013.01); *A61F 13/534* (2013.01); *A61F 2013/530481* (2013.01); *A61F 2013/53472* (2013.01)

(58) Field of Classification Search

CPC .. A61F 13/5323; A61F 13/535; A61F 13/534; A61F 2013/53782; A61F 2013/530481; A61F 13/15585; A61F 13/15699; A61F 13/15617; A61F 13/15634; A61F 13/15658; A61F 13/47; A61F 2013/53472; A61F 13/15642; A61F 13/1565; A61F 13/15674; A61F 13/45

See application file for complete search history.

(56) References Cited

U.S. PATENT DOCUMENTS

| | | | | |
|---|---|---|---|---|
| 6,660,903 B1 * | 12/2003 | Chen | ................. | A61F 13/53704 604/378 |
| 2002/0052587 A1 * | 5/2002 | Magnusson | ........... | A61F 13/535 604/385.101 |
| 2004/0102752 A1 * | 5/2004 | Chen | ................. | A61F 13/53409 604/378 |

(Continued)

FOREIGN PATENT DOCUMENTS

| | | | | |
|---|---|---|---|---|
| CN | 106361501 B * | 3/2020 | ............. | A61L 15/40 |
| EP | 0815817 A1 * | 1/1998 | ....... | A61F 13/47227 |

(Continued)

OTHER PUBLICATIONS

Search Report and Opinion dated May 31, 2023. 6 pages.

*Primary Examiner* — Adam Marcetich
(74) *Attorney, Agent, or Firm* — RMCK Law Group PLC

(57) ABSTRACT

An absorbent structure includes an absorbent pad having cellulose fluff mixed with superabsorbent granular material, and at least one fluff-free absorbent insert inserted in at least one through-opening of the absorbent pad, in which between the fluff-free absorbent insert and a central section of the through-opening two longitudinal channels located on opposite sides of the fluff-free absorbent insert are formed.

10 Claims, 4 Drawing Sheets

(56) References Cited

U.S. PATENT DOCUMENTS

2004/0127870 A1* 7/2004 DiPalma ............... A61F 13/535 604/378
2004/0193127 A1* 9/2004 Hansson ............... A61F 13/535 604/385.01
2007/0078422 A1* 4/2007 Glaug ................... A61F 13/474 604/385.01
2010/0114049 A1* 5/2010 Noda .................... A61F 13/533 604/372
2012/0316526 A1* 12/2012 Rosati .................... A61K 38/10 604/366
2013/0090619 A1* 4/2013 Carbonari ......... A61F 13/15707 604/378
2013/0090620 A1* 4/2013 Carbonari ......... A61F 13/49001 604/378
2013/0231622 A1* 9/2013 Dieringer .......... A61F 13/51108 604/374
2021/0000660 A1* 1/2021 Smet ..................... A61F 13/535

FOREIGN PATENT DOCUMENTS

EP 2949300 A1 12/2015
EP 3153141 A1 4/2017

* cited by examiner

ABSORBENT STRUCTURE FOR SANITARY ARTICLES AND METHOD FOR ITS PRODUCTION

CROSS-REFERENCE TO RELATED APPLICATION

This application claims priority to Italian Patent Application No. 102022000024798 filed Dec. 1, 2022. The disclosure of the above applications is incorporated herein by reference in its entirety.

FIELD OF THE INVENTION

The present invention relates to an absorbent structure for sanitary articles.

The invention was developed in particular with a view to its application for producing absorbent sanitary articles such as, for example, diapers and diaper-pants for babies, incontinence pads for adults, sanitary towels for women, and similar sanitary articles intended to absorb body fluids.

The absorbent structure according to the present invention may also be used for producing plasters and similar sanitary articles for covering wounds.

According to another aspect, the invention relates to a method for producing an absorbent structure for sanitary articles.

DESCRIPTION OF THE PRIOR ART

Absorbent sanitary articles typically have a layered structure comprising an outer sheet or backsheet impervious to liquids, an inner sheet or topsheet permeable to liquids and intended to be placed in contact with the user's skin, and an absorbent structure that has the function of capturing and storing body fluids.

The absorbent structure often comprises superabsorbent granular materials. These superabsorbent materials are known by various names such as, for example, SAP (Super Absorbent Polymer) or AGM (Absorbent Gelling Material). In most cases, hydro-gelling materials are used that are capable of absorbing and capturing liquids.

Most absorbent structures of absorbent sanitary articles currently on the market belong to one of the following two categories:

- absorbent core formed by cellulose fluff, obtained from defibrated cellulose, mixed with superabsorbent granular material;
- fluff-free absorbent core formed by one or more non-woven webs with superabsorbent granular material deposited on the surface or trapped inside the non-woven webs.

In recent years there has been a strong demand for more flexible, thinner, lighter and more absorbent sanitary articles, and this has led to the development of fluff-free absorbent cores which have gradually been employed to replace absorbent cores formed from cellulose fluff mixed with superabsorbent granular material.

EP-A-3153141 by the same applicant describes a method for producing a fluff-free absorbent structure for absorbent sanitary articles, wherein superabsorbent granular material is distributed on a non-woven layer with fibers bound by hot air (Air Through Bonding or ATB), and wherein the non-woven layer is volumized by means of a toothed portion that raises and opens the fibers to favor the penetration of the particles of superabsorbent material inside the bound fibers of the non-woven layer.

The evolution of the market towards fluff-free absorbent cores has prompted many manufacturers of absorbent sanitary articles and raw materials to develop sheets of ATB (Air Through Bonding) material, which are more suitable for producing absorbent cores in terms of capacity to trap particles of SAP and in terms of softness to give softness to the absorbent core in the absence of cellulose fluff. To fulfill these functions, ATB materials must be very bulky and, therefore, the sheets are very thick, and this leads to several problems, including:

- the transport of these materials is not very efficient because the mass/volume ratio is very low;
- the duration of the reels in the machine is very low and involves problems related to frequent reel changes.

Furthermore, fluff-free absorbent cores generally have a high absorbency, and the absorbent core may expand several times its weight and volume. These increases may cause the absorbent article to deform and/or sag in the crotch region as they become saturated with liquid. This may cause leaks through the edges of the absorbent core.

EP3453368A1 discloses an absorbent core comprising cellulose fluff, or fluff-free, wrapped between a topsheet and a backsheet, wherein at least one attachment zone is provided between the absorbent core, the topsheet and the backsheet, in which no absorbent material is present.

OBJECT AND SUMMARY OF THE INVENTION

The object of the present invention is to provide an absorbent structure that overcomes the problems of the prior art.

According to the present invention, this object is achieved by an absorbent structure having the characteristics forming the subject of claim 1.

According to another aspect, the invention relates to a method for producing an absorbent structure having the characteristics forming the subject of claim 8.

The claims form an integral part of the technical disclosure provided in relation to the invention.

BRIEF DESCRIPTION OF THE DRAWINGS

The invention will now be described in detail with reference to the attached drawings, given purely by way of non-limiting example, wherein.

It will be appreciated that the various figures may not be represented on the same scale. It will also be appreciated that some elements or components may not be illustrated to make other elements/components more visible and to simplify the understanding of the figures.

DETAILED DESCRIPTION

Figure 1:
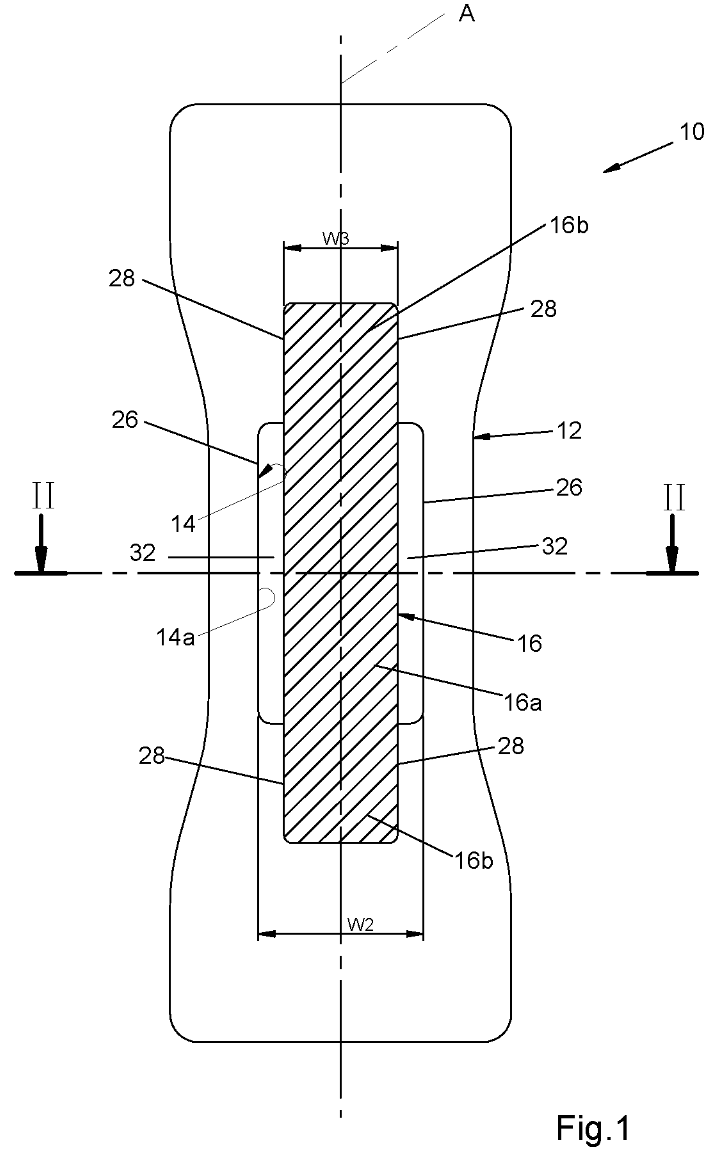
FIG. 1 is a plan schematic view of an embodiment of an absorbent structure according to the present invention.
Figure 2:
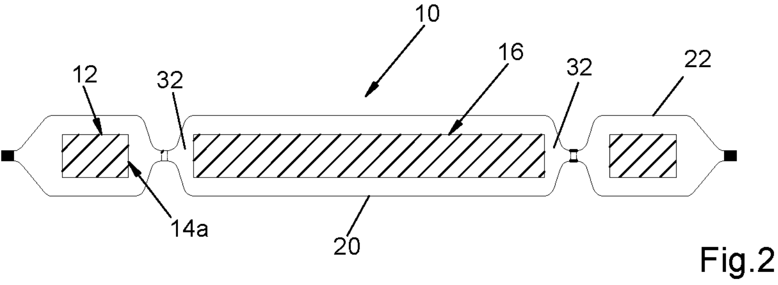
FIG. 2 is a schematic cross-section along the line II-II of FIG. 1.

With reference to FIGS. 1 and 2, numeral 10 indicates an absorbent structure according to the present invention.

The absorbent structure 10 comprises an absorbent pad 12 comprising cellulose fluff. The absorbent pad 12 may be formed exclusively of cellulose fluff or of a mixture of cellulose fluff and superabsorbent material. The superabsorbent material may be granular or in fibers (Super Absorbent Fibers or SAF). The absorbent pad 12 has an elongated shape along a longitudinal axis A and has at least one through-opening 14.

The absorbent structure 10 comprises at least one fluff-free absorbent insert 16 inserted in the through-opening 14 of the absorbent pad 12, so that the fluff-free absorbent insert 16 is surrounded by cellulose fluff, optionally mixed with superabsorbent material.

The fluff-free absorbent insert 16 is formed by a non-woven layer wherein the superabsorbent material is incorporated. The superabsorbent material contained in the fluff-free 16 absorbent insert can be granular or in fiber (SAF).

The fluff-free 16 absorbent insert may comprise fibers normally used for producing non-woven webs such as:

- synthetic fibers such as polyester, polyethylene, polypropylene, polyurethane, polyamide, acrylate, cellulose acetate, cupro, lyocell, modal, viscose or rayon, or their mixtures, or
- natural fibers such as cotton, linen, hemp, jute, ramie, coconut, pineapple, gorse, hibiscus, straw, bamboo, soy, kapok, *eucalyptus*, or their mixtures.

Figure 3:
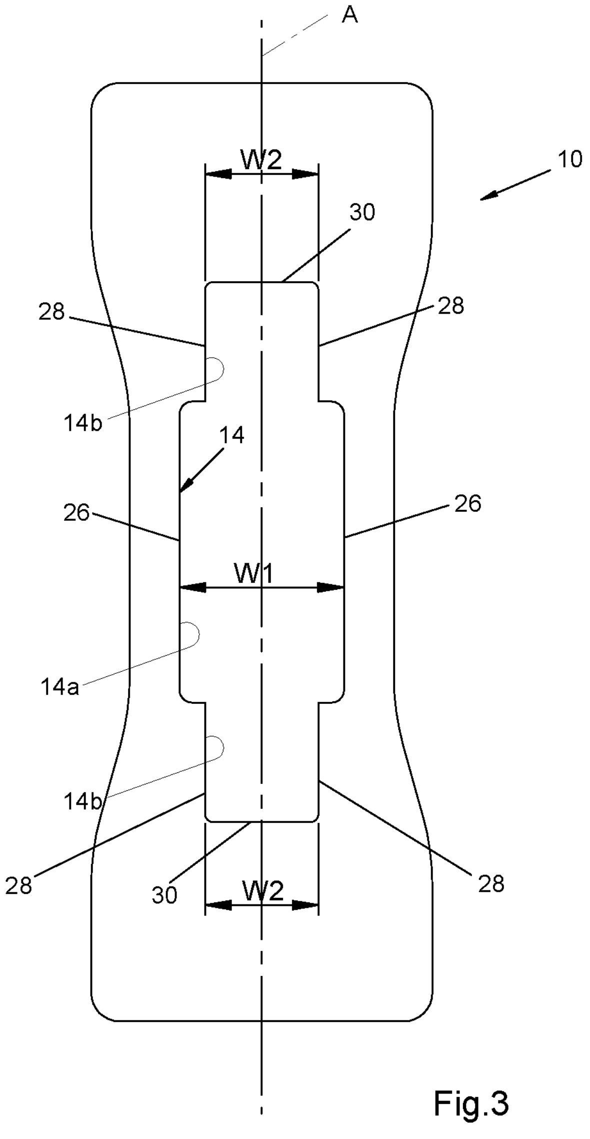
FIG. 3 is a schematic plan view of the absorbent structure of FIG. 1 without the absorbent insert.

With reference to FIG. 3, the through-opening 14 is elongated along the longitudinal axis A and has a central section 14*a* and two end sections 14*b* located on opposite sides of the central section 14*a*.

The central section 14*a* has a width W1 greater than the width W2 of each of the two end sections 14*b*. The central section 14*a* and the two end sections 14*b* have respective longitudinal edges 26, 28. In the embodiment illustrated in the figures, the longitudinal edges 26, 28 are straight and parallel to the longitudinal axis A. In possible embodiments the longitudinal edges 26, 28 may have different shapes, for example curved.

The two end sections 14*b* have respective transverse edges 30. In the embodiment illustrated in the figures, the transverse edges 30 are straight and perpendicular to the longitudinal axis A. In possible embodiments, the transverse edges 30 may have different shapes, for example curved.

The longitudinal edges 26, 28 and the transverse edges 30 cumulatively define a perimeter edge of the through-opening 14.

With reference to FIG. 1, the fluff-free absorbent insert 16 has an elongated shape in the longitudinal direction A and has a central section 16*a* and two end sections 16*b* located on opposite sides of the central section 16*a*. The central section 16*a* and the two end sections 16*b* of the fluff-free absorbent insert 16 are housed, respectively, in the central section 14*a* and in the respective end sections 14*b* of the through-opening 14.

In the embodiment illustrated in the figures, the fluff-free absorbent insert 16 has a rectangular shape with two longitudinal edges that are straight and parallel to the longitudinal axis A. In possible embodiments the longitudinal edges of the fluff-free absorbent insert 16 may have different shapes, for example curved.

In possible embodiments, the fluff-free absorbent insert 16 has a width W3 substantially equal to the width W1 of the end sections 14*b* of the through-opening 14. The width W3 of the fluff-free absorbent insert 16 may be constant along the longitudinal axis A.

Two longitudinal channels 32 located on opposite sides of the fluff-free absorbent insert 16 are formed between the fluff-free absorbent insert 16 and the longitudinal edges 26 of the central section 14*a* of the through-opening 14. Each of the longitudinal channels 32 has a width equal to (W1−W3)/2. Each of the longitudinal channels 32 may have a width between 0.1 mm and 70 mm.

This arrangement guarantees centering of the fluff-free absorbent insert 16 with respect to the absorbent pad 12 and allows the formation of longitudinal channels 32 that are symmetrical with respect to the longitudinal axis A, and of a large width.

In a possible embodiment, each of the longitudinal channels 32 may have at least one curved longitudinal side. This can be achieved by shaping the longitudinal edges 26 of the central section 14*a* of the through-opening 14 and/or the longitudinal edges of the central section 16*a* of the fluff-free absorbent insert 16 according to a curved shape.

With reference to FIG. 2, the absorbent structure 10 may comprise two non-woven webs 20, 22, which enclose the absorbent pad 12 and at least one fluff-free absorbent insert 16 in a sandwich-like manner. The two non-woven webs 20, 22 may be fixed together along the outer perimeter of the absorbent pad 12 and through the longitudinal channels 32. The fastening between the two non-woven webs 20, 22 may be carried out by welding (thermal or ultrasonic) or by glue.

The absorbent structure 10 may comprise at least one acquisition and distribution layer (not illustrated in the figures) arranged on a surface of the assembly formed by the absorbent pad 12 and by at least one fluff-free absorbent insert 16. The acquisition and distribution layer, if present, has the object of uniformly distributing the liquids on the surfaces of the absorbent pad 12 and of the fluff-free absorbent insert 16, and may consist of one or more layers of high-volume non-woven fabric, for example, Air Through Bonding, free from absorbent material.

The absorbent structure 10 may be included in an absorbent sanitary article and may be sandwiched between a backsheet and a topsheet, as is usual in the field of production of absorbent sanitary articles.

Figure 4:
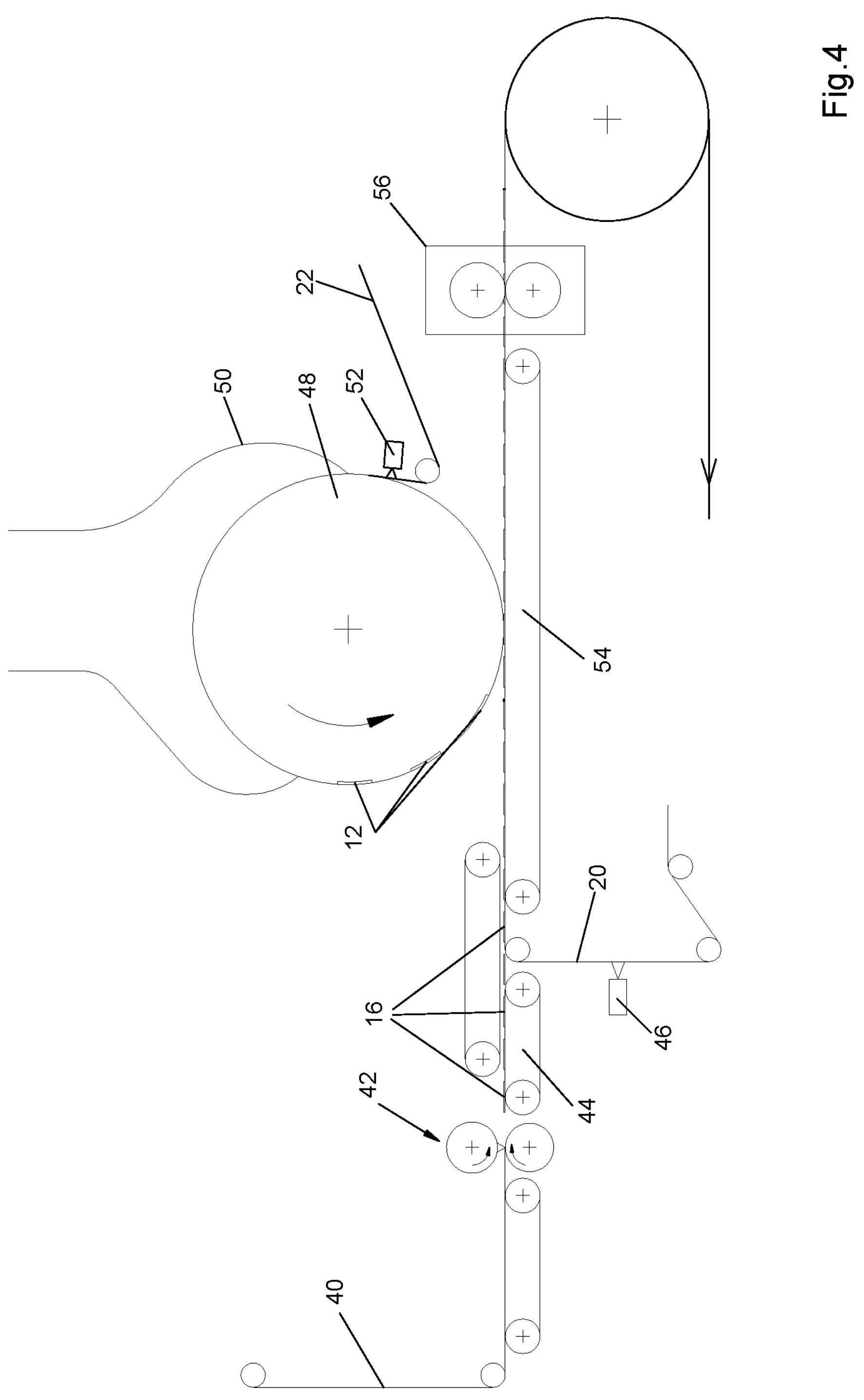
FIG. 4 is a schematic view illustrating an embodiment of a method for producing absorbent structures according to the present invention.

FIG. 4 schematically illustrates a method for producing an absorbent structure 10 as previously described.

The method comprises forming an array of fluff-free absorbent inserts 16 comprising a non-woven layer in which superabsorbent material is incorporated.

The array of fluff-free absorbent inserts 16 is obtained starting from a continuous fluff-free absorbent web 40 formed by one or more non-woven layers wherein fibrous or granular superabsorbent material is incorporated.

The fibers used for producing the continuous fluff-free absorbent web 40 may be joined together mechanically (for example, by needle punching), with adhesives or with thermal processes, using conventional techniques in the sector, such as Air Through Bonding, Spunbond, Meltblown, etc.

The superabsorbent material may be granular and may be dispersed among the fibers of the continuous fluff-free absorbent web 40, for example, with the techniques described in WO2022/034468 and EP-A-3153141 by the same Applicant. The superabsorbent material may also be in the form of fibers (superabsorbent fibers or SAF) mixed with the fluff-free fibers.

In a possible embodiment, the continuous fluff-free absorbent web 40 may be formed off-line and collected in reels that feed the apparatus for producing absorbent structures. In a possible embodiment, the continuous fluff-free absorbent web 40 may be formed by an apparatus (for example, as described in WO2022/034468 or EP-A-3153141) arranged in-line with the apparatus for producing absorbent structures.

The continuous fluff-free absorbent web 40 is cut transversely in a cutting unit 42 so as to form an array of fluff-free absorbent inserts 16 that advance spaced apart on a conveyor 44.

The fluff-free absorbent inserts 16 may be fixed on a first continuous non-woven web 20 in mutually spaced apart positions along a longitudinal direction. A glue dispenser 46 may be provided to apply glue onto the first continuous non-woven web 20 in phase with the fluff-free absorbent inserts 16.

The method for producing absorbent structures 10 comprises forming an array of absorbent pads 12 having respective through-openings 14 having the form illustrated in FIG. 3. The absorbent pads 12 may be formed from cellulose fluff or from a mixture of cellulose fluff and superabsorbent material, in granular form and/or in fibers (SAF).

The array of absorbent pads 12 may be produced, for example, as described in EP-A-2775975 by the same Applicant. The apparatus for forming the absorbent pads 12 may comprise a forming wheel 48 rotatable around a rotation axis, and provided with seats with a shape corresponding to the shape of the absorbent pads 12. The forming wheel 48 may face a chamber 50 containing cellulose fluff and possibly granular or fibrous superabsorbent polymers. The mixture of cellulose fluff and superabsorbent polymers is applied to the seats of the forming wheel 48, and may be retained in the seats by suction. The chamber 50 may only contain cellulose fluff and the superabsorbent material, if provided, may be applied to the cellulose fluff deposited in the seats of the forming wheel 48 by a dosing device.

A second continuous non-woven web 22 may be applied to the forming wheel 48 upstream of the chamber 50. The absorbent pads 12 may be formed and fixed to the second continuous non-woven web 22 in mutually spaced apart positions along a longitudinal direction. This attachment may be obtained by glue applied to the second continuous non-woven web 22 by a glue dispenser 52.

The method for producing absorbent structures 10 envisages arranging the absorbent pads 12 and the fluff-free absorbent inserts 16 in phase with each other and inserting the fluff-free absorbent inserts 16 into respective through-openings 14 of the absorbent pads 12, so as to form an array of absorbent structures 10, each of which comprises an absorbent pad 12 and at least one fluff-free absorbent insert 16 inserted into a respective through-opening of the respective absorbent pad 12.

The forming wheel 48 transfers the absorbent pads 12 onto a conveyor 54 in phase with the fluff-free absorbent inserts 16, so that during the transfer of the absorbent pads 12 from the forming wheel 48 to the conveyor 54, the fluff-free absorbent inserts 16 fit into the respective through-openings of the respective absorbent pads 12.

The forming wheel 48 may overlap the second non-woven web 22—on which the absorbent pads 12 are fixed—to the first non-woven web 20, on which the fluff-free absorbent inserts 16 are fixed. During the overlapping of the first and second continuous non-woven webs 20, 22, the fluff-free absorbent inserts 16 are inserted into respective through-openings 14 of the absorbent pads 12, and the array of absorbent pads 12 and fluff-free absorbent inserts 16 is sandwiched between the first and second continuous non-woven web 20, 22.

Between the fluff-free absorbent inserts 16 and the respective central sections of the through-openings 14 of the absorbent pads 12 there is a distance such that longitudinal through-channels 32 are formed (FIG. 1), as previously described.

The array of absorbent structures 10 thus formed may be sent to a welding unit 56 that welds together the first and second continuous non-woven webs 20, 22 along the perimeter of the absorbent pads 12 and along the longitudinal channels 32, thereby forming absorbent structures 10, as illustrated in FIGS. 1 and 2.

The array of absorbent structures 10 thus formed may be fixed onto a continuous backsheet web. Then, a continuous topsheet web may be applied over the continuous backsheet web so as to sandwich together the array of absorbent structures 10 between the continuous topsheet and backsheet webs.

Figure 5:
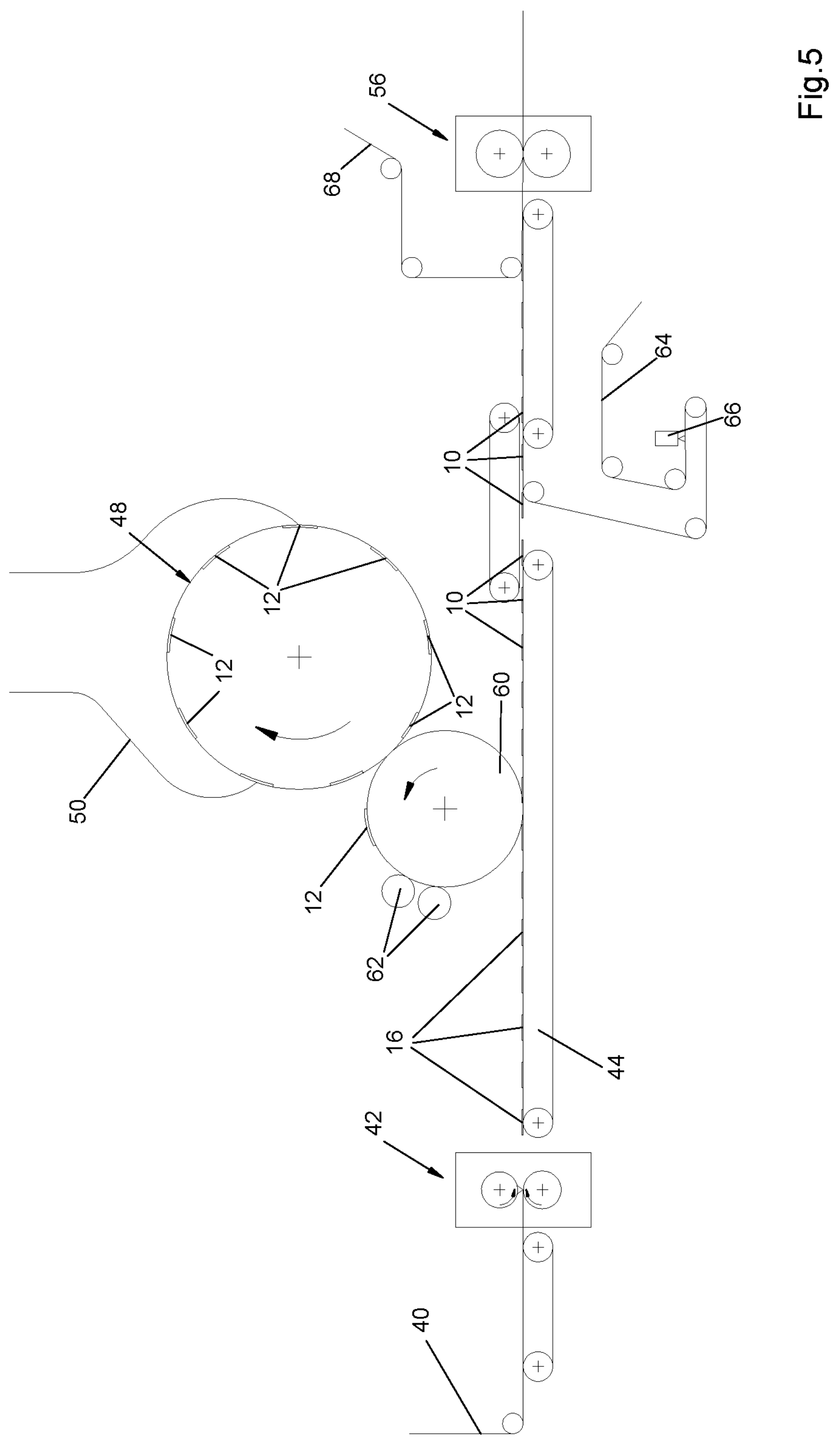
FIG. 5 is a schematic view illustrating a second embodiment of a method for producing absorbent structures according to the present invention.

FIG. 5 illustrates a second embodiment of a method for producing absorbent structures 10.

In the embodiment of FIG. 5 the absorbent pads 12 and the fluff-free absorbent inserts 16 may not be enclosed between two non-woven webs. The array of absorbent pads 12 formed on the forming wheel 48 may be transferred to a transfer wheel 60, and may be compressed on the transfer wheel 60 by compression rollers 62. The transfer wheel 60 applies the absorbent pads 12 on the conveyor 44 in phase with the fluff-free absorbent inserts 16, so that during the transfer of the absorbent pads 12 from the transfer wheel 60 to the conveyor 44, the fluff-free absorbent inserts 16 fit into the respective through-openings of the respective absorbent pads 12.

The array of absorbent structures 10 formed by the absorbent pads 12 and by the fluff-free absorbent inserts 16 may be fixed onto a first continuous web 64. The first continuous web 64 may be a backsheet web. A glue dispenser 66 may be provided to apply glue onto the first continuous web 64 in phase with the absorbent structures 10.

Therefore, a second continuous web 68 may be applied onto the first continuous web 64 so as to sandwich the array of absorbent structures 10 between the first and second continuous webs 64, 68. The second continuous web 68 may be a topsheet web.

A welding unit 54 may be provided to weld the first and second continuous webs 64, 68 together around the absorbent structures 10.

The main advantages of the absorbent structure according to the present invention are as follows:

- the perimeter part of the absorbent structure is soft and helps keep the skin dry;
- the fluff-free absorbent insert gives the absorbent structure high integrity and absorbency characteristics;
- the longitudinal channels between the fluff-free absorbent insert and the cellulose fluff pad confer flexibility and improve wearability;
- the absorbent structure has a reduced thickness and is particularly suitable for being included in absorbent sanitary articles for incontinent adults,
- the shape of the through-openings guarantees centering of the fluff-free absorbent insert with respect to the absorbent pad and allows the formation of very wide longitudinal channels.

Of course, without prejudice to the principle of the invention, the details of construction and the embodiments can be widely varied with respect to those described and illustrated, without thereby departing from the scope of the invention as defined by the claims that follow.

The invention claimed is:

1. An absorbent structure, comprising:

an absorbent pad comprising cellulose fluff and having at least one through-opening elongated along a longitudinal axis, wherein said at least one through-opening has a central section and two end sections located on opposite sides of the central section, and wherein the central section has a width greater than a width of each of the end sections, at least one fluff-free absorbent insert comprising a non-woven layer in which superabsorbent material is incorporated, wherein the fluff-free absorbent insert has a shape elongated along said longitudinal axis and has a central section and two end sections located on opposite sides of the central section of the at least one fluff-free absorbent insert, wherein the central section and the two end sections of the at least one fluff-free absorbent insert are housed, respectively, in the central section and in respective end sections of the at least one through-opening, and wherein between the at least one fluff-free absorbent insert and longitudinal edges of the central section of the at least one through-opening, two longitudinal channels are formed located on opposite sides of the at least one fluff-free absorbent insert.

2. The absorbent structure of claim 1, wherein said central section of the at least one through-opening has longitudinal edges that are straight and parallel to the longitudinal axis.

3. The absorbent structure of claim 1, wherein the at least one fluff-free absorbent insert has a width substantially equal to a width of each of said end sections of the at least one fluff-free absorbent insert.

4. The absorbent structure of claim 1, wherein the at least one fluff-free absorbent insert has a constant width along the longitudinal axis.

5. The absorbent structure of claim 1, wherein said central section of said through-opening and/or said central section of said fluff-free absorbent insert have longitudinal edges with a curved shape so that each of said two longitudinal channels has at least one curved longitudinal edge.

6. The absorbent structure of claim 1, comprising two non-woven webs, which sandwich the absorbent pad and said at least one fluff-free absorbent insert.

7. The absorbent structure of claim 6, wherein said two non-woven webs are fixed together through said two longitudinal channels.

8. A method for producing absorbent structures, comprising:

forming an array of absorbent pads comprising cellulose fluff, wherein each of said absorbent pads of the array of absorbent pads has at least one through-opening elongated along a longitudinal axis, wherein said at least one through-opening has a central section and two end sections located on opposite sides of the central section, and wherein the central section has a width greater than a width of each of the end sections, forming an array of fluff-free absorbent inserts comprising at least one non-woven layer in which superabsorbent material is incorporated, wherein said fluff-free absorbent inserts of the array of fluff-free absorbent inserts have a shape elongated along said longitudinal axis and have a central section and two end sections, and placing said fluff-free absorbent inserts within respective through-openings of said absorbent pads so that the central sections and the end sections of the fluff-free absorbent inserts are housed, respectively, in the central sections and in respective end sections of respective through-openings, wherein between said fluff-free absorbent inserts and longitudinal edges of respective central sections of the through-openings, longitudinal channels are formed located on opposite sides of the fluff-free absorbent inserts.

9. The method of claim 8, comprising fixing together first and second continuous non-woven webs through said longitudinal channels.

10. The method of claim 8, wherein said central sections of said through-openings and/or said central sections of said fluff-free absorbent inserts have longitudinal edges with a curved shape so that each of said longitudinal channels has at least one curved longitudinal edge.

* * * * *